(12) United States Patent
Schubert et al.

(10) Patent No.: US 6,740,749 B1
(45) Date of Patent: May 25, 2004

(54) OZONE-INDUCED GENE EXPRESSION IN PLANTS

(75) Inventors: Roland Schubert, Munich (DE);
Heinrich Sandermann, Munich (DE);
Dietrich Ernst, Gaunting (DE);
Rudiger Hain, Langenfeld (DE);
Regina Fischer, Munich (DE)

(73) Assignees: GSF-Forschungszentrum fur Umwelt, Oberschleissheim (DE); Bayer AG, Leverkusen (DE)

( * ) Notice: Subject to any disclaimer, the term of this patent is extended or adjusted under 35 U.S.C. 154(b) by 0 days.

(21) Appl. No.: 09/202,634

(22) PCT Filed: Jun. 18, 1997

(86) PCT No.: PCT/EP97/03187

§ 371 (c)(1),
(2), (4) Date: Mar. 3, 1999

(87) PCT Pub. No.: WO97/49823

PCT Pub. Date: Dec. 31, 1997

(30) Foreign Application Priority Data

| Jun. 25, 1996 | (DE) | 196 25 347 |
| Jun. 25, 1996 | (DE) | 196 25 330 |
| Sep. 2, 1996 | (DE) | 196 25 569 |
| Dec. 27, 1996 | (DE) | 196 54 574 |

(51) Int. Cl.$^7$ .............................................. C07H 21/04
(52) U.S. Cl. .................... 536/24.1; 435/320.1; 536/23.1
(58) Field of Search .................... 536/24.1; 800/278, 800/295; 435/410

(56) References Cited

U.S. PATENT DOCUMENTS 750,386 A * 5/1904 Conkling et al. ......... 435/172.3

5,689,045 A * 11/1997 Logemann et al.

FOREIGN PATENT DOCUMENTS

WO    WO-9964562    * 12/1999

OTHER PUBLICATIONS

Dec. 1994, "Optimierung der heterologen Expression von Stilbensythasegenen fur den Pflanzenschutz" Fischer, R. Doktorarbeit Universitat Hohenheim, Stuttgart, 1994.

Dec. 1991, "Biochemical plant responses to ozone" Rosemann, D. Plant Physiology, Bolume 97, No. 4, pp. 1280–1286.

1994,"Plant devence systems induced by ozone" Kangasjarvi, J. et al., Plant, Cell and Environment, vol. 17, 1994, pp. 783–794.

Jun. 1997 "An ozone–responsive region of the grapevine resveratrol synthase promoter differs from the basal pathogen–responsive sequence" R. Schubert, Plant Molecular Biology, vol. 34, No. 3, pp. 417–426.

* cited by examiner

Primary Examiner—Jeffrey Fredman
Assistant Examiner—Juliet C. Switzer
(74) Attorney, Agent, or Firm—Merchant & Gould, P.C. (23552)

(57) ABSTRACT

The present invention relates to new DNA sequences, a method for producing new plants which contain a new DNA sequence, the coding sequence thereof being expressed after ozone induction. The invention also relates to said new plants and the use of DNA sequences to produce ozone-responsive gene expression in plants and plant cells. Moreover, it relates to a new promoter, the specificity thereof being increased by removal of the ozone response capacity thereof.

2 Claims, 2 Drawing Sheets

FIG. 1

FIG. 2

SEQUENCE LISTING

```
<160> NUMBER OF SEQ ID NOS: 3

<210> SEQ ID NO 1
<211> LENGTH: 161
<212> TYPE: DNA
<213> ORGANISM: Vitis vinifera
<220> FEATURE:
<221> NAME/KEY: unsure
<222> LOCATION: (145)
<223> OTHER INFORMATION: a, c, t, or g

<400> SEQUENCE: 1
acttttcgag cccttgaac tggaaattaa tacattttcc acttgactt tgaaaaggag      60 gcaatcccac gggagggaag ctgctaccaa ccttcgtaat gttaatgaaa tcaaagtcac    120
tcaatgtccg aatttcaaac ctcancaacc caatagccaa t                        161

<210> SEQ ID NO 2
<211> LENGTH: 33
<212> TYPE: DNA
<213> ORGANISM: Vitis vinifera
```

-continued

```
<400> SEQUENCE: 2
ccccaagctt ccccggatca catttctatg agt                    33

<210> SEQ ID NO 3
<211> LENGTH: 34
<212> TYPE: DNA
<213> ORGANISM: Vitis vinifera

<400> SEQUENCE: 3
cgcggatcct caattgaagc cattgatcct agct                   34
```

OZONE-INDUCED GENE EXPRESSION IN PLANTS

This invention relates to new DNA sequences, a method for producing new plants which contain a new DNA sequence, the coding sequence thereof being expressed after ozone induction. The invention also relates to said new plants and the use of DNA sequences to produce ozone-responsive gene expression in plants and plant cells. Moreover, it relates to a new promotor, the specificity of which is increased by removal of the ozone response capacity thereof.

The ozone concentrations in the lower troposphere above the continents of the northern hemisphere have steadily increased over the past one hundred years as a result of greater industrial activities (Volz and Kley (1988) Nature 332, 240–242). Meanwhile, ozone values reach intermittent peak concentrations of 100 nL/L up to nL/L in Europe and North America (Krupa et al. (1995) Environ. Pollut: 87, 119–126).

The phytotoxicity of the air pollutant ozone has been well tested and documented, e.g., in Heagle (1989) Annu. Rev. Phytopathol. 27, 397–423; Heath (1994) in: Alscher, Wellburn (ed) "Plant responses to the gaseous environment", pp. 121–145, Chapman & Hall, London. A decreased net photosynthesis and an increased early senescence are usually the result of such ozone impact which, consequently, results in diminished plant growth and a lower harvest yield.

Although ozone penetrates the plant cell through open stomata by means of diffusion, the ozone concentration in the intercellular spaces of the leaf is almost zero, irrespective of the environmental ozone concentration (Laisk et al. (1989) Plant Physiol. 90, 1163–1167). It is currently assumed that ozone reacts quickly with components of the cell walls and the plasmalemma and is converted into reactive oxygen species, such as peroxide-anions, hydroxyl radicals and hydrogen peroxide which were detected in ozone-treated plant material by using electron spin resonance spectroscopy (Mehlhorn et al. (1990) Physiologia Plantarum 79, 377–383). The so-called "oxidative burst", i.e. the fast development of a relatively high quantity of reactive oxygen species, can lead to a dramatic disturbance of the normal cell function due to alteration of the permeability of the plant membrane, inactivation of redox-sensitive proteins and increased lipid peroxidation.

Recent tests conducted on ozone-treated plants showed an increased biosynthesis of non-specific, defensive enzymes, the function of which is to protect live cells against damage due to oxidative stress (Kangasjärvi et al. (1994) Plant, Cell and Environment 17, 783–794). Yet the signal-transduction chain, which is responsible for the ozone-induced gene activation, which transmits to the cell core the relevant information about the formation of apoplastic, reactive oxygen species, has not been understood up to now. Various factors, such as the increase of calcium concentration in cytosol (Price et al. (1994) The Plant Cell 6, 1301–1310), the formation of salicylic acid (Klessig and Malamy (1994) Plant Mol. Biol. 26, 1439–1458) and the phytohormone jasmon acid (Farmer (1994) Plant Mol. Bio. 26 1423–1437) and ethylene (Ecker (1995) Science 268, 667–674) are currently being discussed as possible signal connections, caused by oxidative stress, which generally play a part in defence reactions of plants.

Tests conducted on ozone-gassed tobacco plants showed that ozone causes an increased expression of various disease-resistant genes, namely a few PR-(pathogenesis-related) proteins (Ernst et al. (1992) Plant Mol. Biol. 20, 673–682; Ernst et al. (1996) J. Plant Physiol. 148, 215–221; Eckey-Kaltenbach et al. (1994) Plant Physiol. 104, 67–74). These results indicate that oxidative stress, caused by ozone, influences the expression and regulation of defensive genes of plants in a similar way as that described regarding pathogenic attack. Only very limited information on cis-regulatory elements and transcription factors, which possibly play a part in the control of gene expression of non-specific defensive genes as a response to various environmental influences, is available at present (Lee et al. (1994) Eur. J. Biochem. 226, 109–114). However, based on previous results, it can be assumed that with respect to the genes coding for PR-proteins, separate or at least only partly overlapping ways of signal transduction exist (Somssich (1994) in: Nover (ed) "Plant promoters and transcription factors", pp. 163–179, Springer Publishing House, Berlin; Dolferus et al. (1994) Plant Physiol. 105, 1075–1087).

With respect to the activity of the stilbene synthase (STS), which takes part in the phytoalexin synthesis, it is known that in adult plants it is induced by environmental stress factors, such as, e.g., pathogenic attack (Langcake (1981) Physiol. Plant Pathol. 18, 213–226), ultraviolet light (Fritzemeier and Kindl (1981) Planta 151, 48–52) and ozone (Rosemann et al. (1991) Plant Physiol. 97, 1280–1286. Contrary to this a constitutive expression pattern was observed in embryos (Sparvoli et al. (1994) Plant Mol. Biol. 24, 743–755).

Stilbene synthase enzymes catalyze the synthesis of stilbenes such as resveratrol or pinosylvin from one molecule of p-cumaroyl-CoA or cinnamoyl-CoA and three units of malonyl-CoA. Resveratrol as well as pinosylvin have photoalexin properties and an antifungal activity, and perform, as phytoalexins in combination with other stilbenes derived from the phenylpropane metabolism, an important function in the defence against pathogens (Hart (1981) Annu. Rev. Phytopathol. 19, 437–458).

STS genes are found in some non-related plant species such as, e.g., peanut (Schröder et al. (1988) Eur. J. Biochem. 172, 161–169), grapevine (Hain et al. (1993) Nature 361, 153–156) and pine (Fliegmann et al. (1992) Plant Mol. Biol. 18, 489–503) and are organized in larger gene families, comprising six or more genes (Lanz et al. (1990) Planta 181, 169–175; Wiese et al. (1994) Plant Mol. Biol. 26, 667–677).

Experiments with transgenic tobacco cells indicate that the expression of the stilbene synthase is regulated mainly at a transcription level, and that the stress-induced signal transduction chain has been preserved in various plant species during the course of evolution (Hain et al. (1990) Plant Mol. Biol.15, 325–335.

STS genes from peanut (*Arachis hypogaea*) and grapevine (*Vitis vinifera*) have already been isolated (Schröder et al. (1988) supra or Hain et al. (1993) supra) and expressed in transgenic plants (Hain et al. (1990) supra or Hain et al. (1993) supra).

DNA sequences coding for stilbene synthase are known, e.g., from European Patent EP 0 309 862, German Patent Application DE-A-41 07 396, European Patent Application 0 464 461, as well as U.S. Pat. No. 5,500,367. These documents describe the isolation of stilbene-synthase genes and their use to produce transgenic plants. The resulting transgenic plants show greater resistance to various plant pests such as fungi, bacteria, insects, viruses and nematodes. Plasmids containing STS genes have been deposited with the German Collection of Microorganisms (DSM), Mascheroder Weg 1B, D-38124 Braunschweig. Also included in the deposition is the VstI-gene from grapevine in the pVstI plasmid, under deposit number DSM 6002 (DE-A-41 07 396, EP-A-0 464 461, U.S. Pat. No. 5,500,367).

While in the meantime also the use of STS coding sequences to produce male, sterile plants and altered blossom colour has been described (German Patent Application DE-A-44 40 200), a possible relation between STS gene expression and ozone induction has remained completely unexplored up to now.

Meanwhile there are various indications that in order to produce an effective as possible resistance to disease, based on the expression of STS genes in transgenic plants, it is advantageous if the expression of the heterologous STS gene (or the heterologous STS genes) in the plant is stimulated first of all by the attacking pathogen, i.e. if it is stimulated first of all by the interaction of plant and pathogen (Fischer and Hain (1994) Current Opinion in Biotechnology 5, 125–130; Fischer (1994) "Optimization of the heterological Expression of Stilbene-synthase Genes for the Protection of Plants", Hohenheim University). This is endorsed particularly by the observation that the pathogen-induced STS gene expression is locally limited to the place of infection and is of a transient nature, which means that the STS expression rises relatively fast to a maximum and declines again in less than 48 hours (Hain et al. (1993) supra). Also experiments conducted on transgenic tobacco plants, in which STS genes were expressed under the constitutive 35S RNA promoter of cauliflower mosaic virus, showed that the resistance to disease achieved in said plants is lower than in plants which expressed the identical genes under the control of the pathogen-inducible homologous STS promotor after fungus infection (Fischer and Hain (1994) supra; Fischer (1994) supra). Anyway, it is desirable that the STS expression in transgenic, cultivated plants which, due to the inserted STS genes show greater resistance to disease, are activated and controlled solely (and not until) by the attack of pathogens and not additionally (or already before) by undesirable environmental stress factors such as ozone.

Thus, it is an important task of biotechnological research of plant protection to realize a more specific expression of defensive genes in plants, in order to be able to materialize molecular biological strategies for producing plants of greater resistance in an efficient and controllable manner. An important aspect in doing so is to eliminate undesirable, non-specific environmental stimuli such as, e.g., the induction of certain defensive genes through ozone, ultraviolet light, heavy metals, extreme temperatures and other abiotic stimuli.

Thus, it is an important object of this invention to make available new DNA sequences which play a direct part in the ozone-induced expression of resistance genes.

Another object of the invention is to show possibilities for removing the ozone induction, i.e. to eliminate undesirable stimulation of the gene expression through ozone.

Furthermore, an important object of this invention is to provide a DNA sequence with the help of which stilbene-synthase genes can be expressed in transgenic plants only after contact of the plant with the pathogen and not through ozone stimulation.

As mentioned already at the outset, a steady increase in ozone impact can be observed which also has drastic effects on vegetation. The observation and determination of ozone concentrations in the air constitute already today a focal point of chemical, physical and biological, environmental research. An important instrument in this context are the so-called biomonitors, with the help of which ozone impact and the consequences thereof, particularly phytotoxic effects can be easily determined both qualitatively and quantitatively.

Thus, a further object of this invention is to provide DNA sequences that can be used to produce targeted ozone-inducible promoters. With the help of such promotors it is possible for so-called reporter genes, the expression of which can be proven by simple, enzymatic tests, and which are well known in biotechnical research, to be used as biomonitors.

Another object of the invention is to provide a system with the help of which certain genes,—whose gene products are able to detoxify oxygen species in cells—can be "turned on", if necessary, as for instance in case of great ozone impact. In other words, by providing DNA sequences, which are responsible for ozone-responsive gene regulation, an ozone-inducible expression of said genes such as, e.g., catalase and/or superoxide-dismutase genes, shall be rendered possible. Thus, it is an object of the invention to make available DNA sequences which can be used for producing an ozone-inducible, cellular "ozone protection system". Further objects of the invention will become apparent as the following description proceeds.

These problems are solved by the subject-matter of the independent claims, based particularly on the provision of the DNA sequences, according to the invention, which are directly involved in the ozone-induced gene expression in plants.

We found, to our surprise, that a certain plant nucleic acid sequence is directly involved in the ozone-responsive STS expression. While experiments with transgenic tobacco embryos and plants—which express the customary reporter gene uidA from *E. coli* that codes for a β-glucuronidase under the control of variously long 5' deletions of the VstI-promoter from grapevine—indicate that at least a few cis-elements, responsible for the fungus induction, are within the range of the promotor which comprises base pairs −140 to −280 (calculated from the start of transcription) (Fischer (1994) supra), the range of the VstI sequence, which comprises base pairs −280 to −430, is essential for a strong activation of the gene expression through ozone. Based on our experiments, it was possible to show that a VstI promoter, which is left with only base pairs up to and including −280 (and which thus is lacking the VstI-promoter sequences, located further upstream) is no longer ozone inducible. As mentioned above, said shortened promotor is nevertheless still able to indicate pathogen-induced gene expression of the coding sequence controlled by same (see Fischer (1994) supra).

Our analyses also lead us to suspect a relation between the treatment of plants with ozone and an increased biosynthesis or release of ethylene in plant cells. Therefore, an involvement of ethylene-responsive elements in the ozone-induced gene expression cannot be excluded. Thus, by taking into consideration familiar cis-elements, which are currently being discussed in connection with ethylene-response capacity (Sessa et al. (1995) Plant Mol. Biol. 28, 145–153; Shinshi et al. (1995) Plant Mol. 27, 923–932), an involvement of the sequence range of the VstI promotor, which comprises base pairs −283 to −273, cannot be excluded in an ozone-induced STS-gene expression.

Accordingly, the ozone-responsive DNA sequence range, which is described here for the first time, comprises base pairs −270 to −430 of the VstI promotor from grapevine.

Thus, the present invention relates to the DNA sequence (SEQ ID NO:1), as defined in Claim 1:

ACTTTTCGAG CCCCTTGAAC TGGAAATTAA TACATTTTCC ACTTGACTTT TGAAAAGGAG GCAATCCCAC GGGAGGGAAG CTGCTACCAA CCTTCGTAAT GTTAATGAAA TCAAAGTCAC TCAATGTCCG AATTTCAAAC CTCANCAACC CAATAGCCAA T, which is essential for the ozone-induced gene expression in plants. A preferred version of the DNA sequence, according to the invention, deals with a DNA sequence, which originates from grapevine, and especially preferred from the stilbene synthase gene VstI from grapevine (base pairs −270 to −430).

Furthermore, the invention relates to a promotor region of the VstI-gene which lacks at least the DNA sequence that comprises base pairs −270 to −430 of the VstI-gene. A preferred version concerns a promotor region of the VstI gene, which only comprises the sequence range from the start of the translation to base pair −270 of the VstI gene. It is particularly preferred that the promoter region, which lacks the sequence range −270 to −430 of the VstI gene, is able to convey a pathogen-induced gene expression in plants.

The invention also relates to chimeric nucleic acid molecules, into which the DNA sequence of base pairs −270 to −430 of the VstI-gene or at least a fragment of this sequence range has been inserted. It is especially preferred that the chimeric nucleic acid molecules, according to the invention, render possible, due to the presence of the DNA sequence of base pairs −270 to −430 of the VstI gene or at least a fragment thereof, an ozone-inducible expression of the coding regions in plants contained therein.

The nucleic acid molecules can be any nucleic acid molecules, especially DNA or RNA molecules, e.g., cDNA, genomic DNA, mRNA, etc. They can be naturally occurring molecules or molecules produced by gene technology or by chemical synthetic processes.

By making available, according to the invention, DNA sequences, promotor regions, nucleic acid molecules or vectors, it is now possible to mutate plant cells by means of gene technology methods in such a way that they show ozone-inducible characteristics. Furthermore, it is now possible to mutate plant cells by means of gene technology methods in such a way that they characterize one or more genes—which are naturally ozone inducible, due to the presence of the DNA sequence set out in Claim No. 1 or a DNA sequence derivable therefrom or one that is homologous with said DNA sequence—as being no longer inducible by ozone but preferably inducible mainly by pathogens.

A special advantage of the invention is the fact that the ozone induction of naturally ozone-inducible genes in plants and plant cells can be eliminated by deleting the DNA sequence, as set out in Claim No. 1, or at least a fragment thereof, in the genes which naturally contain this DNA sequence or a DNA sequence which can be derived therefrom or one that is homologous with said DNA sequence.

Another advantage of the invention is that genes which cannot or cannot substantially be naturally induced through ozone, can be characterized as being ozone inducible by using the invented nucleic acid sequences in plant and plant cells. In a preferred version the nucleic acid sequence, which is responsible for the ozone-inducible expression or at least a fragment thereof, controls the expression of genes, the gene products of which are able to detoxify reactive oxygen species that can develop among other things, as a consequence of ozone in plant cells. In a particularly preferred version, the nucleic acid sequence controls the expression of catalase and/or superoxide-dismutase genes.

In an alternative version, the DNA sequence that is responsible for the ozone-inducible gene expression controls the expression of reporter genes which are measured in order to determine ozone concentrations quantitatively and/or qualitatively and to evaluate the effects of ozone. Such reporter genes can be, e.g., the uidA gene from *E. coli*, which codes for the enzyme β-glucuronidase (GUS), luciferase genes or other genes, customary in plant biotechnology. Every expert in biotechnology, biochemistry or molecular biology is familiar with appropriate reporter genes.

Furthermore, the invention relates to vectors which contain the above-mentioned DNA sequences or promoter regions or fragments thereof. Thus, this invention relates also to vectors, particularly plasmids, cosmids, viruses, bacteriophages and other vectors, common in gene technology, which contain the above-mentioned nucleic acid molecules, according to the invention and which, if required, can be used for transferring said nucleic acid molecules to plants or plant cells.

The invention also relates to transformed microorganisms, such as bacteria, viruses and fungi which contain the nucleic acid sequences, according to the invention.

It is also an object of the invention to provide plants and plant cells which are characterized by the absence of the ozone-inducible expression of genes that are naturally induced in plants through ozone.

This problem is solved by providing the DNA sequence responsible for the ozone induction and by making available promoters which lack said sequence and which for this reason render possible a no longer ozone-inducible gene expression of genes in plant and plant cells controlled by the promotors.

The problem of rendering possible an ozone-responsive gene expression of genes which are not naturally inducible through ozone is likewise solved by providing the DNA sequence, according to the invention. Thus, plants and plant cells are made available which in the presence of ozone specifically define certain characteristics.

A preferred version concerns transformed plants and plant cells in which genes are ozone-inducibly expressed, and the gene products thereof are able to detoxify reactive oxygen species in plant cells. Particular preference is given in this connection to catalase and/or superoxide-dismutase genes. As an alternative, it is possible to produce plants and plant cells (including protoplasts) which characterize so-called reporter genes after induction through ozone and which, if required, can be used as biomonitors.

Thus, the subject-matter of the invention is transgenic plants which contain, integrated in the plant genome, the recombined nucleic acid molecules, as described above. Such plants can, in principle, be any plants. It concerns preferably a monocotyle or dicotyle useful plant. Examples of monocotyle plants are plants which belong to the genuses of Avena (oat), Triticum (wheat), Secale (rye), Hordeum (barley), Oryza (rice), Panicum, Pennisetum, Setaria, Sorghum (millet), Zea (corn). Dicotyle, useful plants are, e.g., cotton, leguminous plants such as legumes, and especially alfalfa, soya bean, rape, tomato, sugar beet, potato, ornamental plants, trees. Other useful plants can be fruit-bearing plants (particularly apples, pears, cherries, grapes, citrus fruits, pineapples and bananas), oil palms, tea and cacao shrubs, tobacco, sisal, as well as medicinal plants, such as rauwolfia and digitalis. Special preference is given to grain, such as wheat, rye, oat, barley, rice, corn and millet, sugar beet, rape, soya, tomato, potato and tobacco.

Furthermore, the subject-matter of the invention is the propagation material of plants, according to the invention, such as, e.g., seeds, fruits, cuttings, tubers, rootstock, etc., as well as constituents of such plants, such as plant cells, protoplasts and calli.

The plant cells include differentiated and non-differentiated plant cells (including protoplasts), as well as plant cells (including protoplasts) in which nucleic acid molecules are integrated in the plant genome or are present as autonomous molecules (including transient transformation).

In another version, the invention relates to host cells, particularly prokaryotic or eukaryontic cells, which have been transformed or inoculated with a recombined nucleic acid molecule or a vector, as described above, and cells which originate from said host cells and which contain the described nucleic acid molecules or vectors. The host cells can be bacteria or fungus cells, as well as plant or animal cells.

The object of this invention is also to show methods for the production of plant and plant cells which are characterized by the lack of an ozone-inducible expression of a gene, the expression thereof in plants and plant cells is naturally stimulated by ozone.

This problem is solved through processes by means of which the production of new plants and plant cells, which do not have this naturally occurring ozone-induced gene expression, is made possible.

As already mentioned above, it is also the object of this invention to provide methods for the production of plants and plant cells which express such genes—the expression of which is naturally not, or not substantially activated by ozone—after ozone stimulation. This problem is solved by methods with the help of which plants and plant cells can be produced which, after the invented DNA sequences or at least a fragment thereof has been inserted into naturally not ozone-inducible genes, or genes which are ozone-inducible only to a minor degree express such genes after ozone stimulation.

There are various methods by which such new plants or plant cells can be produced. For one thing, plants or plant cells can be mutated by conventional gene-technological transformation methods in such a way that the new nucleic acid molecules are being integrated in the plant genome, which means that stable transformants are produced.

According to the invention, plants or plant cells which, due to the absence of the invented nucleic acid sequence or at least a fragment thereof, no longer show an ozone induction of the gene(s) which naturally contains/contain said sequence, are produced by a method which includes the following steps:

a) Deletion of the DNA sequence—as defined in Claim No. 1, or a sequence which can be derived from said sequence, or which is homologous with said sequence, or at least a fragment of such sequence—from a gene which after the deletion of the invented DNA sequence, includes regulatory elements essential for the possibly regulated transcription and translation in plant cells, and has at least one coding sequence, as well as possibly a termination signal for the termination of the transcription and the addition of a poly-A-tail to the respective transcript.

b) Transformation of plant cells with the gene or nucleic acid molecule, produced in step a), and c) possibly the regeneration of transgenic plants and possibly the propagation of the plants.

As an alternative it is possible in step a) that instead of deleting the sequence responsible for the ozone-induction, said sequence or at least a fragment thereof can be inactivated or blocked, e.g., through mutagenesis, and thus remain in the gene in an inactivated form. Irrespective of the manner in which the ozone-responsive gene range is deleted, all manipulative measures can be carried out by means of conventional methods and aids of recombined gene technology (see, e.g., Sambrook et al. (1989) Molecular Cloning: A Laboratory Manual, Second Edition, Cold Spring Harbour Laboratory Press, Cold Spring Harbour, N.Y.).

In a particularly preferred version the nucleic acid molecule, which in step b) is transferred to plants or plant cells, contains regulatory elements which allow, e.g., a pathogen-induced gene expression of the coding sequence.

According to the invention, plants or plant cells which, due to the presence of the invented nucleic acid sequence that is essential or co-responsible for an ozone-induced expression of the genes containing same, or at least a fragment of said sequence, are produced by a method which includes the following steps:

a). Insertion of at least one DNA sequence, according to the invention, which in plants can produce an ozone-induced gene expression, or a sequence which is derivable from said sequence, or which is homologous with said sequence, or at least a fragment of said sequence, in a gene which is not naturally or not substantially expressed as ozone-inducible.

b) Transformation of plant cells by way of the gene or nucleic acid molecule, produced in step a), which has all elements that are naturally required for the expression in plant cells, and c) possibly the regeneration of transgenic plants and perhaps the propagation of plants.

In a preferred version the gene concerned is a catalase dismutase, superoxide-dismutase or a common reporter gene.

Another object of the invention is to show advantageous usage of the invented nucleic acid sequences.

The invention includes, therefore, uses of the new DNA molecules to produce the aforementioned plants and plant cells, according to the invention, which are characterized either by the absence of a certain phenotypical distinguishing mark that is normally influenced by ozone, or which precisely due to the presence of the invented DNA sequence distinguish themselves from non-transgenic plants and plant cells by ozone-induced characteristics.

Furthermore, the invention includes the use of the invented nucleic acid molecules to produce plants which are characterized by an increased pathogen-induced but not an ozone-induced resistance to disease.

The invention also relates to the use of the invented nucleic acid sequences or fragments thereof for detecting and identifying ozone-responsive nucleic acid elements.

The expert can identify such ozone-responsive nucleic acid elements by applying customary molecular biological methods, e.g., hybridizing experiments or DNA protein-binding studies. For example, as a first step, the poly $(A)^+$ RNA is isolated from a tissue which was treated with ozone. Then a cDNA-bank is set up. In a second step and with the help of cDNA-clones, which are based on poly$(A)^+$ RNA molecules from a non-treated tissue, those clones from the first bank are identified by way of hybridizing whose corresponding poly$(A)^+$ RNA molecules are induced strictly in the ozone treatment. With the help of cDNAs identified in this manner, promoters which have ozone-responsive elements are subsequently isolated. The nucleic acid sequences and molecules can be useful instruments when examining and characterizing these isolated promoters.

The subject-matter of the invention includes also nucleic acid molecules or fragments thereof which hybridize with one of the above-described nucleic acid molecules or one of the above-mentioned DNA sequences of the invention. Within the scope of this invention the term "hybridizing" means hybridizing under conventional hybridizing conditions, preferably under stringent conditions, such as are described, for example, in Sambrook et al (1989) Molecular Cloning: A Laboratory Manual, Second Edition, Cold Spring Laboratory Press, Cold Spring Harbor, N.Y.

Nucleic acid molecules which hybridize with the molecules, according to the invention, can be isolated, e.g., from genomic or cDNA banks.

The identification and isolation of such nucleic acid molecules can be accomplished by using the nucleic acid molecules, according to the invention, or fragments of said molecules or the reverse complements of such molecules, e.g., by way of hybridizing according to standard procedure (see, e.g., Sambrook et al, supra).

Thus, the invention relates also to the use of an invented DNA sequence or fragments thereof to identify and isolate homologous sequences from plants or other organisms.

For example, nucleic acid molecules which have exactly or substantially the invented nucleotide sequences or fragments of such sequences can be used as a hybridizing probe. The fragments used as a hybridizing probe can also be synthetic fragments which were produced with the help of customary synthesis techniques and the sequence of which basically corresponds with that of a nucleic acid molecule, according to the invention. Once genes that hybridize with the invented nucleic acid sequences have been identified and isolated, it is necessary to determine the sequence and analyze the properties. To do so, a number of molecular biological, biochemical and biotechnological standard methods are available to the expert.

The molecules that hybridize with the nucleic acid molecules, according to the invention, include also fragments, derivatives and allelic variants of the above-described DNA molecules that contain an ozone-responsive sequence in an active or inactivated form, or which are characterized by the fact that they no longer have such sequence. The term "derivative" means in this context that the sequences of these molecules distinguish themselves from the sequences of the above-described nucleic acid molecules in one or several positions and are to a great extent homologous with said sequences. Homology in this connection means a sequence identity of at least 40%, especially an identity of at least 60%, preferably above 80%, and especially preferable above 90%. The deviations from the above-described nucleic acid molecules can have been caused by deletion, addition, substitution, insertion or recombination.

With respect to the nucleic acid molecules which are homologous with the above-described molecules and which constitute derivatives of such molecules, it concerns usually variants of such molecules that constitute modifications which perform the same biological function. These may concern naturally occurring variations, e.g., sequences from other organisms, or mutations in which these modifications can have occurred naturally or were introduced through specific mutagenesis. Furthermore, the variations may concern synthetically produced sequences. With respect to the allelic variants, these may occur naturally as well as be synthetically produced variants, or variants produced by recombined DNA methods.

To prepare the insertion of foreign genes into higher plants or into the cells thereof, a large number of cloning vectors are available which contain a replication signal for *E. coli* and a marker gene to select transformed bacteria cells. Examples of such vectors are pBR322, pUC-series, M13mp-series, pACYC184, etc. The desired sequence can be inserted into the vector at a suitable restrictive cut. The plasmid obtained is used for the transformation of *E. coli* cells. Transformed *E. coli* cells are cultured in a suitable medium and subsequently harvested and lysed. The plasmid is recovered. Usually restrictive analyses, gel electrophoreses and other biochemical, molecular biological methods are applied as an analyzing method to characterize gained plasmid DNA. After each manipulation the plasmid DNA can be split and the gained DNA fragments can be linked with other DNA sequences. Each plasmid-DNA sequence can be cloned in identical or other plasmids.

Many well-known methods are available to introduce DNA into a plant host cell. The expert can determine, without difficulty, the respectively suitable method. These techniques include the following: the transformation of plant cells with T-DNA by using *Agrobacterium tumefaciens* or *Agrobacterium rhizogenes* as transformation medium, the fusion of protoplasts, the direct gene transfer of isolated DNA in protoplasts, the electroporation of DNA, the introduction of DNA by means of the biolistic method, as well as other possibilities. In doing so, stable, as well as transient tranformants, can be produced.

When injecting and electroporating DNA into plant cells no specific demands per se is made on the plasmids used. The same applies to direct gene transfer. Simple plasmids as, e.g., pUC derivatives, can be used. If, however, whole plants are to be regenerated from cells transformed in this way, the presence of a selectable marker gene is required. The expert is familiar with the usual selection markers, and it does not pose a problem for him to select an appropriate marker. Selection markers in common use are those that make the transformed plant cells resistant to a biocide or an antibiotic, such as kanamycin, G418, bleomycin, hygromycin, methotrexate, glyphosate, streptomycin, sulfonyl-urea, gentamycin or phosphinotricin, etc.

Depending on the method selected for introducing genes into the plant cell, additional DNA sequences may be required. If, for example, the Ti or Ri-plasmid is used for the transformation of the plant cell, at least the right boundary, but frequently, however, the right and left boundary of the T-DNA, contained in the Ti and Ri-plasmid must, as flank region, be linked with the genes to be introduced.

If agrobacteria is used for the transformation, the DNA to be introduced must be cloned in special plasmids, i.e. either in an intermediary or in a binary vector. Due to sequences which are homologous with sequences in the T-DNA, the intermediary vectors can be integrated in the Ti- or Ri-plasmid of the agrobacteria through homologous recombination. In addition, the latter includes the vir-region required for the transfer of the T-DNA. Intermediary vectors cannot replicate in agrobacteria. The intermediary vector can be transferred to *Agrobacterium tumefaciens* (conjugation) by means of a helper plasmid. Binary vectors can replicate in *E. coli* as well as in agrobacteria. They contain a selection-marker gene and a linker or a polylinker which are framed in by the right and left T-DNA boundary region. They can be directly transformed into the agrobacteria (Holster et al (1978) Molecular and General Genetics 163, 181–187). The agrobacterium which serves as host cell shall contain a plasmid that has a vir-region. The vir-region is necessary for transferring the T-DNA to the plant cell. Additional T-DNA can be present. The agrobacterium, transformed in the manner described, is used for the transformation of plant cells.

The use of T-DNA for the transformation of plant cells has been thoroughly studied and is adequately described in EP 120 515; Hoekema in: The Binary Plant Vector System, Offsetdrokkerij Kanters B. V., Alblasserdam (1985) Chapter V; Fraley et al (1993) Crit. Rev. Plant. Sci., 4, 1–46 and An et al (1985) EMBO J. 4, 277–287.

For the transfer of the DNA to the plant cell, plant explantates can be appropriately cultivated with *Agrobacterium tumefaciens* or *Agrobacterium rhizogenes*. Out of the infected plant material (leaf fragments, stem segments, roots, but also protoplasts or suspension-cultivated plant cells) whole plants can be regenerated in a suitable medium which can contain antibiotics or biocides for the selection of transformed cells. The regeneration of plants is carried out according to customary regeneration methods by using familiar culture media. Plants or plant cells obtained in the above-described manner can then be examined for the presence of the introduced DNA. Other possibilities for introducing foreign DNA by applying the biolistic method or through protoplast transformation are known (see, e.g., Willmitzer L. (1993) Transgenic Plants, in: Biotechnology, A Multi-Volume Comprehensive Treatise (H. J. Rehm, G. Reed, A. Pühler, P. Stadler, eds.) Vol. 2, 627–659, V. C. H. Weinheim—New York—Basel—Cambridge).

Although the transformation of dicotyl plants or their cells via Ti-plasmid vector systems and with the help of *Agrobacterium tumefaciens* is well established, new studies indicate that also monocotyl plants or their cells are very receptive to transformation by means of Agrobacterium-based vectors (Chan et al (1993) Plant Mol. Biol. 22, 491–506; Hiei et al (1994) Plant J. 6, 271–282; Deng et al (1990) Science in China 33, 28–34; Wilmink et al (1992) Plant Cell Reports 11, 76–80; May et al (1995) Bio/Technology 13, 486–492; Conner and Domiss (1992) Int. J. Plant Sci. 153, 550–555; Ritchie et al (1993) Transgenic Res. 2, 252–265).

Alternative systems for transforming monocotyl plants or their cells are transformations by means of the biolistic setup (Wan and Lemaux (1994) Plant Physiol. 104, 37–48; Vasil et al (1993) (Bio/Technology 11, 1553–1558; Ritala et al (1994) Plant Mol. Biol. 24, 317–325; Spencer et al (1990) Theor. Appl. Genet. 79, 625–631), the protoplast transformation, the electroporation of partially permeabilized cells and the introduction of DNA by means of glass fibres.

The transformed cells grow within the plant in the usual manner (see also McCormick et al (1986) Plant Cell Reports 5, 81–84). The resulting plants can be cultivated normally and grafted with plants which have the same, transformed genetic trait or other genetic traits. The resulting hybrid individual plants have the respective phenotypical properties.

Two or more generations should be cultivated in order to ensure that the phenotypical characteristic is firmly maintained and propagated. Seeds should also be harvested in order to ensure that the respective phenotype or other characteristics are maintained.

By applying the usual methods, transgenic lines can be determined, which are homozygous for the new nucleic acid molecules and, furthermore, their phenotypical behaviour can be examined for an existing or non-existing ozone-response capacity and compared to that of hemizygous lines.

Naturally, plant cells which contain the nucleic acid molecules, according to the invention, can also be further cultivated as plant cells, (including protoplasts, calli, suspension cultures, etc.).

Another object of this invention is the use of the nucleic acid molecules, according to the invention, or fragments of such molecules, or the reverse complements of such molecules to identify and isolate homologous molecules which include ozone-responsive elements from plants or other organisms. As to the definition of the term "homology", please refer to the definition given earlier in the text.

The following examples serve the purpose of explaining the invention.

EXAMPLES

Example 1

Construction of the 5'-Deletions of the VstI Promotor as GUS Fusion Structure in Binary Vector pPCV002

The 5' non-coding sequence range of the VstI gene from grapevine, which hereinafter is referred to as promoter, consists of 1570 base pairs. This promoter, the sequence of which is known from the German Patent Application DE 41 07 396 and Fischer (1994) supra, was amplified as a template with the help of the usual polymerase chain reaction by using the following oligonucleotides as primer and the plasmid pVstI, containing the complete VstI gene (DE-A-41 07 396; Fischer (1994) supra):

5'-CCCCAAGCTT CCCCGGATCA CATTTCTATG AGT-3' (Primer 1, SEQ ID NO: 2)

5'-CGCGGATCCT CAATTGAAGC CATTGATCCT AGCT-3' (Primer 2, SEQ ID NO: 3).

The PCR was carried out according to the protocol of Perking Elmer (Norwalk, USA) by using the native Taq DNA polymerase by Perkin Elmer. The DNA fragment, amplified under usual PCR conditions, was subsequently recut with the restrictive enzymes HindIII (this restrictive cut is found at the 5'-end of primer 1) and BamHI (this restrictive cut is found at the 5'-end of primer 2) and together with the BamHI/EcoRI-fragment from vector pBI101.2 (Jefferson (1987) Plant Mol. Biol. Reporter 5, 387–405), which contains the β-glucuronidase reporter gene (GUS, uidA) from *E. coli*, as well as the termination signal of the nos-gene from *A. tumefaciens*, subcloned into the pUC18-plasmid (Yanisch-Perron et al. (1985) Gene 33, 103–119; available, e.g., from Boehringer Mannheim) via the HindIII and EcoRI-restrictive cuts of the pUC18-polylinker. All cloning steps were carried out by using customary molecular biological methods and aids (for example, Sambrook et al. (1989) supra); restrictive enzymes and other enzymes used for the cloning were acquired from Boehringer Mannheim. The resulting clone (pUC-VstI/GUS) thus contains a translation fusion of the VstI promotor with the GUS gene, in which the first five STS codons in the reading frame are linked with the GUS gene via a BamHI cut. The sequence range of the fusion transition, as well as the sequence of the VstI promotor were checked for their correctness by means of the enzymatic chain-stop method (Sanger et al. (1977) Proc. Natl. Acad. Sci. USA 74, 5463–5467) by using the T7 sequencing kit of Pharmacia (Freiburg).

The cloning of the 5'-deletion mutants in binary vector pPCV002 (Koncz and Schell (1986) Mol. Gen. Genet. 204, 383–396) will be explained below. In most cases pUC18-subclones were used as intermediate vectors, because the smaller pUC plasmid is easier to handle in comparison to the relatively large binary vectors.

Figure 1:
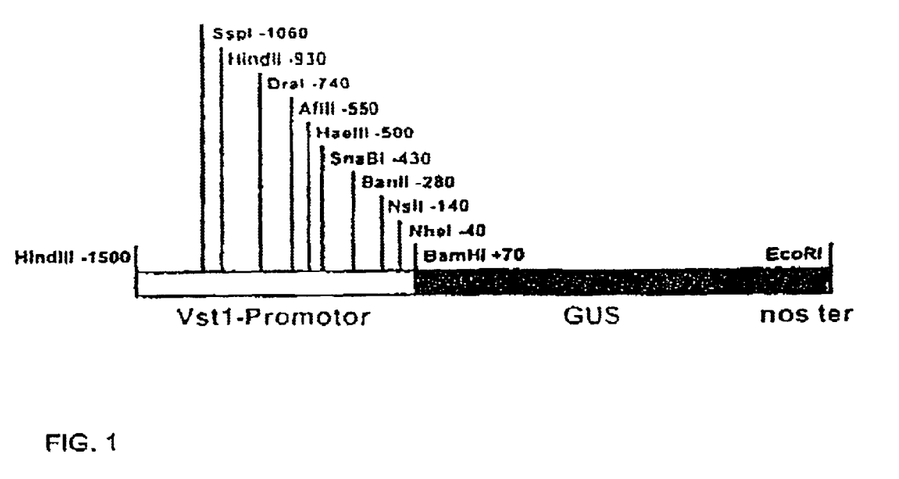

The plasmid designations result from the approximate length of the respective promotor fragment, calculated from the start of the transcription, located at a distance of 73 base pairs from the starting codon (Hain et al. (1993) supra; Fischer (1994) supra). The restricted cuts used for the gradual shortening of the VstI promotor, are diagrammatically shown in Illustration 1.

p1500GUS: The HindIII/EcoRI fragment, which contains the complete STS promotor together with the GUS gene, was isolated from the above described plasmid pUC-VstI/GUS and inserted into the polylinker of pPCV002, between restrictive cuts HindIII and EcoRI.

p1060GUS: A 1130 Bp-promoter fragment was isolated from pUC-VstI/GUS via restrictive cuts BamHI and SspI and cloned in BamHI/HincII-linearized pUC18 (→pUC1130). The GUS gene as BamHI/EcoRI fragment was subsequently isolated from pUC-VstI/GUS and cloned between the BamHI cut and the EcoRI cut of pUC1130.

Finally, the fusion was isolated via HindIII/EcoRI double digestion and inserted into the poylinker of pPCV002 via the same cuts.

p930GUS: The 1.0 kb-promoter fragment was isolated from pUC-VstI/GUS via restrictive enzymes BamHI and HincII and inserted into the polylinker of pUC18 (→pUC1000), via the same cuts. This was followed by cloning analogous to p1060GUS.

p740GUS: The approximately 1.6-kb-long HindIII/BamHI promoter fragment was isolated from plasmid pUC-VstI/GUS and digested with the restrictive enzyme DraI. The resulting 810-Bp-long BamHT/DraI fragment was subsequently cloned in pUC18 via restriction cuts BamHI and HincII (→pUC810). The GUS gene, as a BamHI/EcoRI-fragment, was then isolated from pUC-VstI/GUS and cloned between the BamHi cut and the EcoRI cut of pUC810. Finally, the fusion was isolated via HindIII/EcoRI double digestion and inserted into the polylinker of pPCV002, via the same cuts.

p550GUS: pUC-VstI/GUS was digested with the restrictive enzyme AF1II and the projecting 5' ends were filled up with Klenow enzyme (by Boehringer Mannheim; dNTPs, likewise from Boehringer Mannheim) according to the manufacturer's instructions. This was followed by re-cutting with the restrictive enzyme BamHI, and the resulting 620 Bp-promotor fragment was ligated in BamHI/HincII linearized pUC18 (→pUC620). Then the cloning was continued analogous to that of p1060GUS.

p500GUS: A 570-Bp-long promoter fragment was isolated from pUC-VstI/GUS via a BamHI/HaeIII double digestion and ligated in BamHI/HincII-linearized pUC19-vector (→pUC570). This was followed by further cloning analogous to that for the production of p1060GUS.

p430GUS: Plasmid pUC1000, as described above, was linearized by using the restrictive enzyme SnaBI and subsequently digested with HincII. The linearized vector was subsequently religated whereby the 500 base pairs of the promotor were deleted between –930 and –430 (→pUC500). Further cloning was carried out analogous to pUC106GUS.

p280GUS: pUC-VstI/GUS was digested with the restrictive enzyme BanII and the projecting ends were filled up with Klenow enzyme, and the linearized vector was subsequently digested with the restriction enzyme BamHI. After isolating the 350-Bp-long blunt end/BamHI-promoter fragment, cloning was continued analogous to p1060GUS.

p140GUS: The above-described pUC subclone pUC620 was digested with the restriction enzymes NsiI and PstI, and the linearized vector was subsequently cleaned and religated. This resulted in the deletion of promotor sequences –550 to –140 (→pUC210). The GUS gene, as a BamHI/EcoRI fragment, was subsequently isolated from pUC-VstI/GUS and cloned between the BamHI cut and the EcoRI cut of pUC1130. Finally, the fusion was isolated via a HindIII/EcoRI double digestion and inserted into the polylinker of pPCV002 via the same cuts.

p40GUS: The 110 Bp-promoter fragment together with the GUS gene were isolated from pUC-VstI/GUS by a NheI/EcoRI double digestion, and the fragment was subsequently cloned in XbaI/EcoRI-linearized pPCV002.

pΔGUS: The structure p1500GUS was digested with the restrictive enzyme BamHI, and the cleaned vector was subsequently religated. Thus, the entire promotor fragment was eliminated through the BamHI cut which vector pPCV002 contains naturally in its multiple cloning spot, beside the HindIII cut (Koncz and Schell (1986) supra).

P35SGUS: The fusion of the 35S RNA promotor from cauliflower mosaic virus with the GUS gene, which served as positive control, was isolated as HindIII fragment from the expression vector pRT99GUS (T öpfer et al. (1988) Nucleic Acid Research 16, 8725) and inserted into the multiple cloning spot of pPCV002.

Example 2

Plant Material, Plant Transformation and Regeneration of Transgenic Plants

*Nicotiana tabacum* cv. Petit Havana SR1 (Maliga et al. (1973) Nature New Biol. 244, 29–30) was cultivated as sterile scion culture on hormone-free 1/2 LS-medium (Linsmaier and Skoog (1965) Physiol. Plant 18, 100–127) with 1% saccharose at 26° C., 3000 lux and a 16-hour photoperiod. At 6 to 8-week intervals, sprout segments were transferred to a fresh LS medium. For the transformation of leaf slices with *Agrobacterium tumefaciens* (Horsch et al. (1985) Science 227 1229–1231) 2 to 3-cm-long leaves of sterile scion cultures were stamped into slices of 1 cm in diameter and incubated for 5 minutes with a suspension of agrobacteria (approximately $10^9$ cells/mL YEB medium), which contained one of the above-mentioned plasmid structures. The inoculated leaf segments were kept on a hormone-free LS medium for 2 to 3 days at 26° C. During this time, the bacteria overgrew the leaf segments, which were subsequently washed in liquid LS medium with no hormones and placed on LS-medium with kanamycin (75 µg/mL; Sigma, Munich), cefotaxim (500 µL/mL; Hoechst, Frankfurt) and benzylaminopurine (BAP, 0.5 mg/L; Duchef, Haarlem, The Netherlands). After 2 to 3 weeks, transformed sprouts were visible, which grew roots on hormone-free LS medium with 75 µg/mL kanamycin and 100 µg/mL cefotaxim.

The agrobacteria cultures used for the transformation of the tobacco-leaf segments were produced as follows: First of all the above-described pPCV002 derivatives were inserted into the *E. coli* mobilizing strain S17-1 (Simon et al (1983) Bio/Technology 1, 784–790). This produced competent S17-1 *E. coli* cells, as well as the transformation of the competent cells with the respective plasmids according to Taketo (1988) Biochem. Biophys. Acta 949, 318–324 or Hanahan (1983) J. Mol. Biol. 166, 557–580. Subsequently, the *E. coli* strain, containing the respective binary vector, and the *Agrobacterium tumefaciens*-strain GV3101 C58C1 Rif pMP90RK (Koncz and Schell (1986) supra) were cultured in relevant media up to $OD_{580}$=1.0. The following were used for the cultivation of the *E. coil* bacteria: the customary YT medium (Miller (1972) Experiments in Molecular Genetics, Cold Spring Harbor Laboratory Press, Cold Spring Harbor, N.Y.); bacto-tryptone 0.8% (w/v), yeast extract 0.5% (w/v), NaCl 0.5% (w/v. pH 7.0) at 37° C. For the cultivation of *A. tumefaciens* bacteria, YEB medium (beef extract 0.5% (w/v), yeast extract 0.1% (w/v), bacto-peptone 0.5% (w/v), saccharose 0.5% (w/v), MgSO$_4$ 2 mM, pH 7.2) were used at 28° C. For the subsequent conjugation, the bacteria was separated by centrifuging at 1500×g for 5 minutes and washed twice in freshly prepared 10 mM MgSO$_4$ solution. Then donor (E. coli) and acceptor (A. tumefaciens) were mixed at a ratio of 1:1 and dripped onto a YEB agar plate. After incubation of 16 hours at 28° C., the bacterial drop was rinsed with 10 mM MgSO$_4$ solution and $10^{-2}$, $10^{-3}$ and $10^{-4}$ dilutions were plated out on YEB selection plates. From a single culture an agrobacterial culture was cultivated at 28° C. which was used for the transformation of N. tabacum.

The transgenic tobacco sprouts, which contained one of the above-described VstI promotor/GUS fusions respectively, were propagated via sprout culture, and partially transferred to soil and cultivated in the greenhouse under normal conditions (22° C., 60% relative atmospheric humidity, approximately 15,000 lux) up to blooming. The blossoms were protected against foreign pollination by means of parchment bags, and ripe seed capsules with seeds of the F1-generation were harvested after 4 to 6 weeks. For biological tests in the greenhouse, the seed of the F1-generation was laid out on LS medium with 75 μg/mL of kanamycin. This was done, under sterile conditions, directly out of the capsule or after sterilization of the surface (1. washing briefly with sterile water; 2. incubation for 2 minutes in 70% ethanol; 3. incubation for 10 minutes in 3% NaOCl (13% active chlorine); 4. washing three times with water; 5. drying in the laminar air flow of the safety work bank). After cultivation for about two weeks on LS medium with 75 μg/mL kanamycin at 25–26° C., 2000–3000 lux and an atmospheric moisture of 60%, it was possible to clearly distinguish kanamycin-resistant tobacco embryos and kanamycin-sensitive tobacco embryos. Compared to sensitive embryos, resistant embryos showed a pronounced primary root growth. Aside from the cotyledons, primary leaves were recognizable after two weeks only in the resistant embryos. At this "four-leaf stage" the resistant F1-embryos were transferred to soil, hardened and further cultivated under appropriate conditions.

Example 3

Plant Cultivation, Ozone-treatment and Harvesting of Leaves

For the subsequent ozone-treatment, transgenic, kanamycin-resistant tobacco embryos were first of all transferred from agar-plates into flower pots with a 2:1 mixture of standard substrate (type T/Frühstorfer/Lauterbach) and pearlit and incubated for three weeks in a climatic chamber with a 12-hour-day/night cycle, 15,000 lux, at a day-time temperature of 25° C. and a night-time temperature of 20° C., and at 65 to 70% atmospheric humidity and filtered air.

The tobacco plants were subsequently subjected to a single-ozone pulse for 10 hours and then incubated for 2–14 hours in pollution-free, filtered air. All gassing experiments were conducted under specified climatic conditions, in closed plexiglass boxes which were put into the climatic chamber. The ozone treatments started always at 9:00 a.m. and extended over the cycle of the day. The ozone was produced by electric discharge in dry oxygen. The dosing and analyses were carried out under computer control (Langebartels et al. (1991) Plant Physiol. 95, 882–889). The tobacco leaves of a plant were counted, starting from the top to the bottom of the plant, and were then classified into leaf numbers 1–10, in which the first leaf was at least 8 cm large. The tobacco leaves (classified from 1 to 10) were individually frozen in liquid nitrogen at various points in time after the start of the ozone-treatment and stored at −80° C.

Example 4

β-Glucuronidase Activity Test

The fluorometric analysis of the GUS-enzyme activity was made strictly according to Jefferson (1987) supra or Jefferson et al. (1987) EMBO J. 6, 3901–3907 by using 4-methyl-umbelliferyl-glucuronide (MUG, sigma, Munich). The concentration of the product 4-methylumbelliferon (MU) was measured with a fluorescent photometer (Perkin Elmer LS-2 B filterfluorimeter) in a quartz flow cuvette. The GUS activity in plant extracts was calculated in pmol MU×mg$^{-1}$×min$^{-1}$. The protein concentration in the tobacco leaf extracts was determined according to Bradford (1976) Analyt. Biochem. 72, 248–254.

Parallel conducted experiments with ozone-treated grapevine plants and subsequent Northern Blot analyses showed that gassing with 0.2 μL/L and 0.4 μL/L ozone resulted in a substantial induction of the STS-gene expression on an mRNA plane. For this reason STS genes from grapevine should be particularly well suited to identify ozone-responsive DNA elements. It should be mentioned at this point that genes which have shown up to now a significant, reliably measurable ozone induction in ozone-treated plants as compared to untreated plants are not available.

Figure 2:
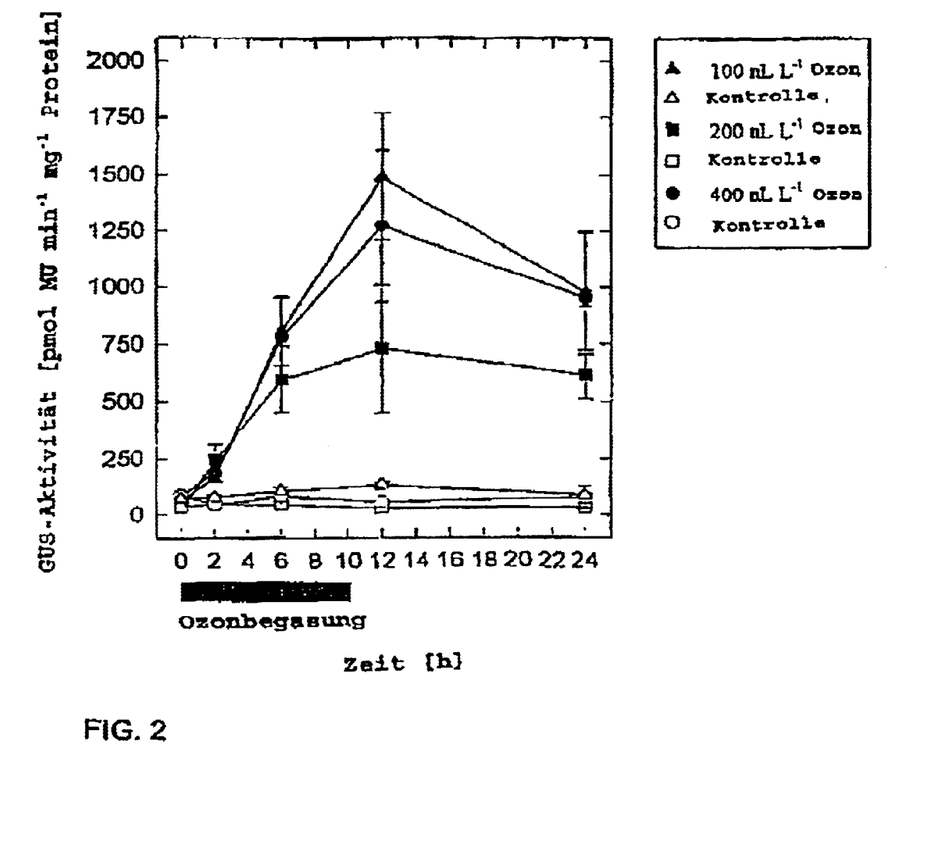

In order to be able to analyze the influence of ozone on a promotor plane, F1-tobacco plants (11 weeks old) of the firmly transformed tobacco line, which contains the VstI promotor/GUS fusion structure with the complete promotor region (p1500GUS), was used in experiments of ozone gassing. GUS-enzyme activities were determined fluorometrically in raw extracts of leaves which were harvested at various times during a 10-hour subjection to ozone gassing with various concentrations of ozone (0.1 μL/L ozone, 0.2 μL/L ozone or 0.4 μL/L ozone) and a 14-hour post-incubation phase in unpolluted air. The results shown in Illustration 2 show a fast ozone-induced increase of the GUS activity as compared to control plants which were kept in only pollution-free air. Thus, the treatment with 0.1 μL/L of ozone caused an 11-fold induction, and the treatment with 0.2 or 0.4 μL/L of ozone even caused an up to 25-fold induction of the expression of the GUS gene, controlled by the STS promotor, 12 hours after the start of the ozone treatment.

For the identification of cis-regulatory sequences, which are responsible for the great ozone induction of the STS promotor that has been observed, the transgenic tobacco lines, which contain the above-described 5'-deletions of the VstI promotor in fusion with the bacterial GUS-reporter genes, were analyzed as independent F0-plants in ozone-gassing experiments. The primary regenerated plants were cultivated in sterile culture for several months and propagated via scion culture. Also F1 tobacco plants (11 weeks old) of these stable transformants were examined for ozone-induced GUS expression.

The transgenic tobacco plants were treated with 0.1 μL/L of ozone for 10 hours and subsequently incubated in unpolluted air for another 2 hours. The GUS activity was determined in raw extracts of medium-old leaves and compared with the enzyme activity in untreated control plants. The results of the fluorometric analysis of the GUS-enzyme activities are shown in Table 1. While the GUS activity results in a slight decrease of the ozone induction (induction factor drops from about 12 (−1500) to about 10 (−430) as the promotor range progressively shortens from −1500 to −430 in ozone-treated test plants as well as in untreated control plants, the additional deletion of the promotor range between −430 and −280, produces a drastic reduction of the GUS expression in ozone-treated test plants. While plants, in which the GUS gene is under the control of the −430-5'-deletion promoter, show a 10-fold ozone-induction compared to control plants, plants in which the GUS-gene is controlled by the shorter −280-5'-deletion promotor, show only a maximum 2-fold induction of the GUS expression through ozone. Consequently, the promotor range of the VstI gene from grapevine, which comprises base pairs −430 to −280, contains cis-active elements which are essential for a pronounced ozone-induced expression of the STS gene.

These results were confirmed by plant cells which contain the above-mentioned structures and which were cultivated in plant-cell cultures.

ILLUSTRATIONS AND TABLES

Illustration 1

Restriction card of the VstI-promotor/GUS-translation fusion in plasmid pUC-VstI/GUS. The plasmid contains a translation fusion of the VstI promotor from grapevine with the GUS gene from *E. coli*. The restrictive cuts used for the cloning of the 5'-deletion mutants have been plotted. nos ter=terminal signal of the nopalinsynthase gene from *Agrobacterium tumefaciens*.

Illustration 2

Kinetics of the VstI promotor-controlled induction of the GUS expression in transgenic F1-tobacco plants, which contain a translation fusion of the GUS gene with the complete VstI promoter from grapevine (p1500GUS) through various concentrations of ozone.

The GUS activities were determined fluorometrically in raw extracts of tobacco leaves (leaf No. 4) according to Jefferson (1987), supra. The various harvesting times can be ascertained from the illustration. The 10-hour ozone treatment was followed by a 14-hour post-incubation of the tobacco plants in unpolluted air. Control plants were only kept in unpolluted air (without ozone gassing). n=3 or 4; mean values±standard errors; all tests were carried out as double experiments.

Table 1

GUs-enzyme activities were determined fluorometrically in protein extracts of medium-old leaves of ozone-treated (+) and untreated (−), independent tobacco transformants.

The transgenic tobacco lines contain various 5'-deletions of the VstI-promotor in fusion with the bacterial GUS-reporter gene. FO-transformants and F1-plants (11 weeks old) were gassed with 100 nL/L of ozone for 10 hours and subsequently post-incubated for 2 hours in unpolluted air. Mean values±standard errors; all analyses were carried out as double experiments

| VstI promotor 5'-deleted to position | Examined, independent, transgenic, tobacco lines | GUS-enzyme activity | | induction factor |
|---|---|---|---|---|
| | | [pmol MU $min^{-1}$ + ozone | $mg^{-1}$ protein] − ozone | |
| −1500 | 1F(1) | 735 ± 100 | 63 ± 7 | 11.7 |
| −740 | 2(F1) | 388 ± 59 | 30 ± 5 | 12.9 |
| −550 | 3(F0) | 126 ± 13 | 12 ± 3 | 10.5 |
| | 2(F1) | 173 ± 25 | 15 ± 3 | 11.5 |
| −500 | 5(F0) | 148 ± 52 | 15 ± 6 | 9.9 |
| −430 | 6(F0) | 141 ± 38 | 14 ± 4 | 10.0 |
| −280 | 6(F0) | 22 ± 4 | 13 ± 3 | 1.7 |
| | 2(F1) | 30 ± 3 | 15 ± 3 | 2.0 |
| −140 | 2(F0) | 12 ± 0.2 | 8 ± 3 | 1.5 |
| | 3(F1) | 24 ± 3 | 15 ± 3 | 1.6 |
| −40 | 3(F1) | 24 ± 2 | 15 ± 3 | 1.6 |
| +70 | 1(F1) | 3.5 ± 1 | 3.5 ± 1 | 1.0 |

What is claimed is:

1. An isolated nucleic acid consisting of the sequence SEQ ID NO: 1, and which conveys an ozone-inducible gene expression.

2. The isolated nucleic acid of claim 1, which originates from grapevine (*Vitis vinifera*).

* * * * *